US012616782B2

(12) United States Patent
Cheng et al.

(10) Patent No.: US 12,616,782 B2
(45) Date of Patent: May 5, 2026

(54) USE OF MITOCHONDRIA TO TREAT AND/OR PREVENT TENDON INJURY OR ITS RELATED DISEASE

(71) Applicant: Taiwan Mitochondrion Applied Technology Co., Ltd., Zubbei City (TW)

(72) Inventors: Han-Chung Cheng, Zubbei City (TW); Chih-Kai Hsu, Zubbei City (TW); Hui-Ching Tseng, Zubbei City (TW); An-Ling Cheng, Zubbei City (TW)

(73) Assignee: TAIWAN MITOCHONDRION APPLIED TECHNOLOGY CO., LTD., Zhubei City (TW)

( * ) Notice: Subject to any disclaimer, the term of this patent is extended or adjusted under 35 U.S.C. 154(b) by 762 days.

(21) Appl. No.: 17/912,458

(22) PCT Filed: Mar. 19, 2021

(86) PCT No.: PCT/CN2021/081687
§ 371 (c)(1),
(2) Date: Sep. 16, 2022

(87) PCT Pub. No.: WO2021/185342
PCT Pub. Date: Sep. 23, 2021

(65) Prior Publication Data
US 2023/0165899 A1 Jun. 1, 2023

Related U.S. Application Data

(60) Provisional application No. 62/992,546, filed on Mar. 20, 2020.

(51) Int. Cl.
| | |
|---|---|
| *A61K 35/19* | (2015.01) |
| *A61K 35/12* | (2015.01) |
| *A61K 35/16* | (2015.01) |
| *A61K 35/28* | (2015.01) |
| *A61K 38/36* | (2006.01) |
| *A61M 1/02* | (2006.01) |
| *A61M 1/36* | (2006.01) |
| *A61P 13/12* | (2006.01) |
| *A61P 17/02* | (2006.01) |
| *A61P 19/02* | (2006.01) |
| *A61P 19/04* | (2006.01) |
| *C12N 5/00* | (2006.01) |
| *C12N 5/073* | (2010.01) |
| *C12N 5/0775* | (2010.01) |

(52) U.S. Cl.
CPC ............ *A61M 1/029* (2013.01); *A61K 35/12* (2013.01); *A61K 35/16* (2013.01); *A61K 35/19* (2013.01); *A61K 35/28* (2013.01); *A61K 38/36* (2013.01); *A61M 1/3693* (2013.01); *A61P 13/12* (2018.01); *A61P 17/02* (2018.01); *A61P 19/02* (2018.01); *A61P 19/04* (2018.01); *C12N 5/0018* (2013.01); *C12N 5/0605* (2013.01);

*C12N 5/0667* (2013.01); *C12N 2500/84* (2013.01); *C12N 2501/998* (2013.01); *C12N 2502/115* (2013.01)

(58) Field of Classification Search
CPC ........ A61K 35/15; A61K 35/16; A61K 35/19; A61K 38/18–1875; A61M 1/029; A61P 19/02; A61P 19/04
See application file for complete search history.

(56) References Cited

U.S. PATENT DOCUMENTS

2021/0379104 A1* 12/2021 Choi ...................... A61K 35/28

FOREIGN PATENT DOCUMENTS

| | | | | | |
|---|---|---|---|---|---|
| CA | 2659673 | A1 * | 1/2008 | ............. | A61P 43/00 |
| CA | 2916190 | A1 * | 9/2014 | ............. | A61P 19/02 |
| CN | 105030647 | | 11/2015 | | |
| CN | 105520891 | A | 4/2016 | | |
| WO | WO 86/03122 | | * 6/1986 | ............. | A61K 35/14 |
| WO | WO-2014147622 | A1 * | 9/2014 | ............. | A61P 19/02 |
| WO | WO2020091463 | A1 | 5/2022 | | |

OTHER PUBLICATIONS

Glas et al. "Quantitative Study of Mitochondria in Rat Liver" J Cell Biol. Jun. 1966;29(3):507-23. doi: 10.1083/jcb.29.3.507 (Year: 1966).*
Gagnon et al. "Effects of calcium and thrombin on growth factor release from platelet concentrates: Kinetics and regulation of endothelial cell proliferation" Biomaterials 25 (2004) 4489-4502 (Year: 2004).*
Tyagi et al. "Platelet Mitochondrial Fusion and Function in Vascular Integrity" Circulation Research. 2024;134:162-164 (Year: 2024).*
Verheul et al. "Platelet: Transporter of Vascular Endothelial Growth Factor" Clinical Cancer Research vol. 3, 2187-2190, Dec. 1997 (Year: 1997).*
Wynendaele et al. "Vascular endothelial growth factor measured in platelet poor plasma allows optimal separation between cancer patients and volunteers: A key to study an angiogenic marker in vivo?" Annals of Oncology 10: 965-971, 1999. (Year: 1999).*

(Continued)

*Primary Examiner* — Thane Underdahl
(74) *Attorney, Agent, or Firm* — MUNCY, GEISSLER, OLDS & LOWE, P.C.

(57) ABSTRACT

The present invention provides a second use of mitochondria, which can cure a tendon injury-related disease and prevent a disease caused by a tendon injury. Specifically, the mitochondria disclosed in the present invention have the effect of repairing injured tendon cells and accelerating the healing of the tendon cells. Therefore, by administering a predetermined amount of mitochondria or a composition containing a predetermined amount of mitochondria to a part with a tendon injury, wound healing of the part with the tendon injury can be promoted, thus achieving the effect of repairing the injured tendon and further preventing a joint disease caused by the tendon injury or inflammation.

12 Claims, 4 Drawing Sheets

(56) References Cited

OTHER PUBLICATIONS

Lyras et al. "Experimental study of tendon healing early phase: Is IGF-1 expression influenced by platelet rich plasma gel?" Orthopaedics & Traumatology: Surgery & Research (2010) 96, 381-387 (Year: 2010).*

MedlinePlus "Tendinitis" URL of this page: //medlineplus.gov/ency/article/001229.htm, 4pages, 2024 (Year: 2024).*

Liu, Yijun Et.al., Research Progress of Platelet-rich Plasma on the Repair of Musculoskelectal System Injury, Acta Universitatis Medicinalis Anhui, Mar. 31, 2017, p. 461 and p. 463, vol. 52, No. 3.

Hu Chaoran Et al., Application research progress of platelet-rich plasma in tendinopathy, Guizhou Medicine, Feb. 28, 2018, p. 173, vol. 42, No. 2.

Hou, Xiao Dong Et.al.,Progress in the Application of Platelet-rich Plasma in the Treatment of Ligament and Tendon Injures, Guangdong Medicine, Sep. 9, 2016, p. 2675 and p. 2677, vol. 37, Issue 17.

Chen Li Et al., Effect of Mitochondria on Wound Repair, Chinese Journal of Aesthetic Medicine. Nov. 2018.vol. 27. No. 11, Nov. 15, 2018, pp. 167-168.

Yu-Ting Su, Study of Human Adipose-Derived Stem Cells on rat model of Rotator Cuff tendinitis, Retrieved from https://hdl.handle.net/11296/bsb95n, on Aug. 25, 2022, 4 pages.

Ji Min Lee et al., Exogenous mitochondrial transplantation improves tendon regeneration via modulating apoptosis signaling, 2019 Korean Society of Bioengineering Spring Conference & International Symposium, https://www.dbpia.co.kr/Journal/articleDetail?nodeId=NODE08580410, p. 420.

* cited by examiner

USE OF MITOCHONDRIA TO TREAT AND/OR PREVENT TENDON INJURY OR ITS RELATED DISEASE

TECHNICAL FIELD

The present invention relates to a second use of mitochondria, and in particular to a use of mitochondria to treat and/or prevent a tendon injury or its related disease.

BACKGROUND

Tendons are dense connective tissues that link bones and muscles together, which can transfer muscle power to bones and enable joint movement. Therefore, the place where the muscle connects to the tendon or the place where the tendon connects to the bone may bear a relatively great mechanical load, such that the above areas are prone to injury, thus affecting the function of the tendon. Tendon injuries usually occur in people who overuse their tendons, repeat similar movements over a long period of time, and repeatedly and excessively press or pull their tendons, leading to tendon tear. If the injury fails to heal, the tendon will become less flexible and is unable to withstand tension. In this case, a tendon lesion is likely to occur and the patient cannot exert force or feels a pain in the part where the lesion occurs, such as biceps tendonitis, rotator shoulder tendonitis, knee patellar tendonitis, Achilles tendonitis, calcific tendonitis, lateral epicondylitis, internal humeral epicondylitis, a ligament injury, ligament inflammation, or the like.

The repair and slow alleviation of the tendon injury often requires long-term treatment or rehabilitation. In order to improve the treatment efficiency, regenerative therapy, such as the platelet-rich plasma (PRP) proliferative therapy, is currently used clinically for the repair of the tendon, ligament, and muscle injuries. That is, by administering PRP to apart with a tendon injury, the injured part of the tendon can be healed efficiently. However, the PRP proliferative therapy is not effective in all patients with the tendon injury. That is, when the patient has the poor coagulation function or the tendon is too severely injured, the PRP treatment has a limited effect.

Because tendon and ligament injuries are common health problems today, it is in urgent need to provide an effective method or composition that can improve the treatment efficiency.

SUMMARY

The main objective of the present invention is to provide a second use of mitochondria. Because a certain amount of mitochondria can repair injured tendon cells, alleviate or inhibit the inflammatory response of the tendon cells, and improve the healing rate of the tendon cells, when a person has a tendon injury-related disease or symptom, the tendon injury-related disease can be treated and/or a joint disease caused by the tendon injury can be prevented by administering a certain amount of mitochondria or a composition containing the mitochondria.

Another objective of the present invention is to provide a composition that contains mitochondria and other substances containing a growth factor, which can greatly improve the efficiency of repairing the tendon cells or alleviating inflammation of the tendon cells, so as to reduce the chance of complications related to a tendon injury or inflammation.

In order to achieve the foregoing objectives, an example of the present invention discloses a composition that contains mitochondria and a blood product, where the blood product contains at least one growth factor.

The blood product is platelet-rich plasma (hereinafter PRP), and the PRP contains a variety of growth factors, such as PDGF-BB, IGF-1, TGF-β1, VEGF, bFGF, etc.

For example, the composition disclosed in the present invention contains mitochondria and PRP, where the dose of the mitochondria ranges from 5 μg to 80 μg and preferably from 15 μg to 40 μg; and the concentration of PRP is preferably 5 v/v % (vol %) or more.

Another example of the present invention discloses a use of mitochondria to prepare a composition for treating a tendon injury-related disease or preventing a joint disease. Therefore, by administering a certain amount of mitochondria to a part with a tendon injury, the repair of the tendon injury can be accelerated and tendon inflammation can be alleviated, thus achieving the effect of treating the tendon injury-related disease or preventing the joint disease.

The dose of the mitochondria in the composition is 40 μg or more.

In order to improve the efficiency of treating the tendon injury-related disease or preventing the joint disease or a ligament injury-related disease, in an example of the present invention, the composition further contains PRP, where the concentration of the PRP is 5% or more, and the composition is preferably composed of PRP with the concentration of 5% or more and mitochondria with the dose of 40 μg or more.

In an example of the present invention, the joint disease or ligament injury-related disease is caused by a tendon injury or tendon inflammation, such as arthritis, joint inflammation, ligament inflammation, a ligament injury, etc.

In an example of the present invention, the tendon injury-related disease is a tendon lesion, tendonitis, or any disease having a symptom of tendon inflammation or swelling, such as biceps tendonitis, rotator shoulder tendonitis, patellar tendonitis of the knee, Achilles tendonitis, calcific tendonitis, lateral epicondylitis, internal humeral epicondylitis, a ligament injury, ligament inflammation, or the like.

In the examples of the present invention, the mitochondria are separated out from autologous or heterologous cells, and are further separated out from stem cells, such as adipose-derived stem cells, mesenchymal stem cells, CD34+hematopoietic stem cells, bone stem cells, umbilical stem cells, amniotic stem cells, amniotic fluid stem cells, placental stem cells, iPS, or neural stem cells.

The beneficial effect of the present invention is that:

The present invention provides the use of mitochondria for treating and/or preventing tendon injury or related disease thereof. The mitochondria or a composition containing mitochondria, such as a composition composed of mitochondria and PRP, does have the ability of improving inflammation or swelling of tendon, and can promote the efficiency of tendon repair to recover the strength and elasticity of the damaged tendon in a short time, so as to achieve the effects of treating or preventing tendon injury-related diseases; the mitochondria or a composition containing the mitochondria of the present invention can promote or accelerate the healing of tendon wounds, so as to achieve the effect of accelerating the repair of damaged tenocytes or treating tendinopathy.

DETAILED DESCRIPTION OF THE EMBODIMENTS

Figure 1:
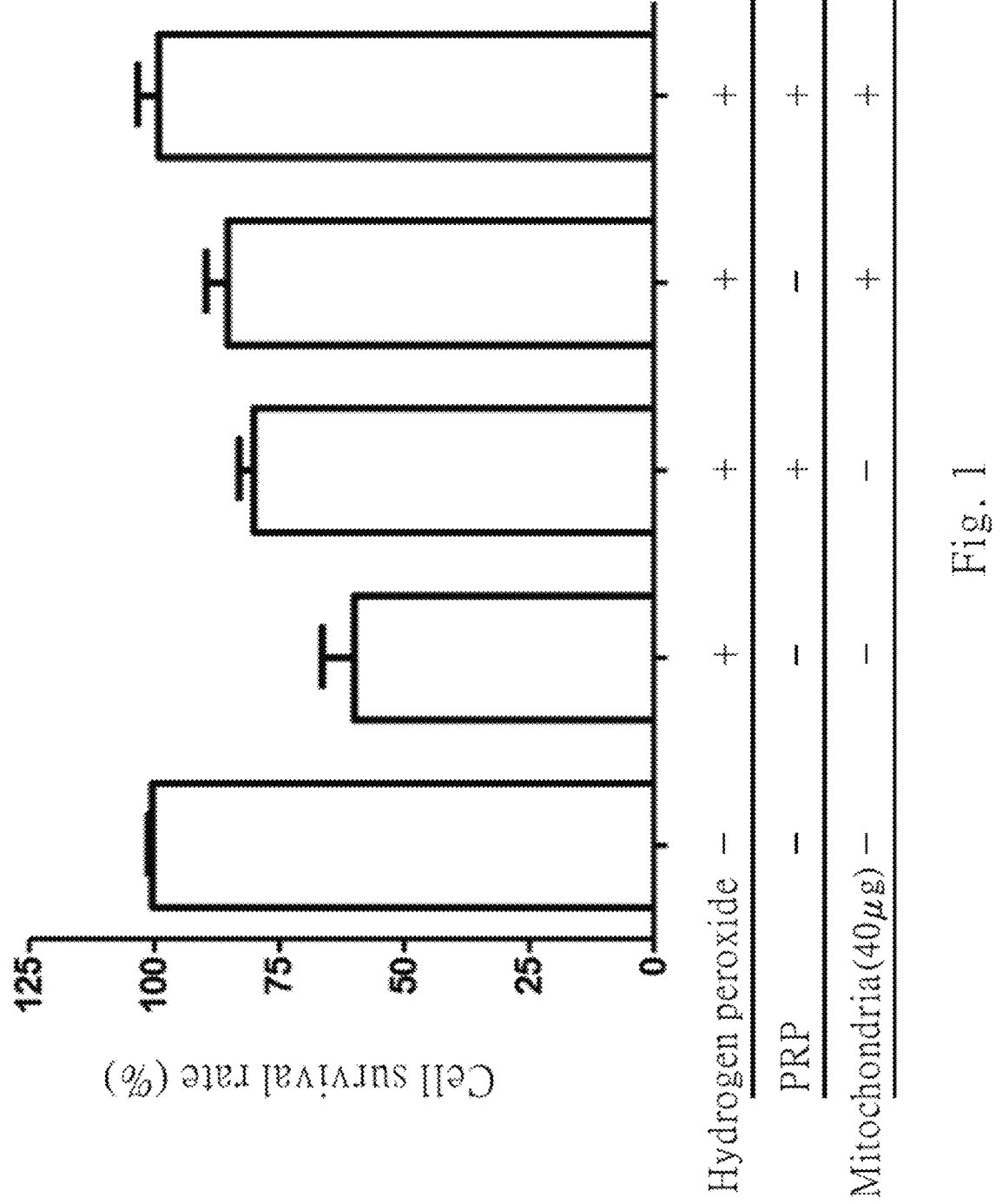
FIG. 1 shows an analysis result of a cell survival rate after the human tendon cells are treated with hydrogen peroxide and then cultured in different administration conditions.

The present invention discloses a second use of mitochondria, which can treat a tendon injury-related disease and prevent a disease caused by a tendon injury. Specifically, the mitochondria disclosed in the present invention have the effect of repairing the injured tendon cells and accelerating the healing of the tendon cells. Therefore, by administering a predetermined amount of mitochondria or a composition containing a predetermined amount of mitochondria to a part with a tendon injury, the wound in this part can be healed, thus achieving the effect of repairing the injured tendon and preventing the occurrence of a joint disease caused by a tendon injury or inflammation.

Generally speaking, the administration dose of the mitochondria ranges from 5 μg to 80 μg, such as 5 μg, 15 μg, 20 μg, 25 μg, 30 μg, 40 μg, 55 μg, 60 μg, 70 μg, or 80 μg. Moreover, the mitochondria can be mixed with different components to prepare a composition, where the mitochondria are preferably mixed with a growth factor or a mixture containing a growth factor. For example, the mitochondria, and PRP or a component containing a growth factor, such as a blood product, are mixed to form a composition.

Further, the mitochondria disclosed in the present invention need to be mixed with another component before being administered to the injured part. For example, the mitochondria mixed with PRP can greatly accelerate the healing of the part with a tendon injury.

The "composition" mentioned in the present invention refers to a material containing an effective dose of mitochondria, and is prepared in different forms and dosage forms according to use requirements or methods, and is formed by necessarily mixing different components, carriers, excipients, or the like.

The "mitochondria" mentioned in the present invention are separated out from cells, and the used separation technique or method should be able to maintain the structural and functional integrity of the mitochondria. For those of ordinary skill in the art to which the present invention pertains, the separation technique or method may be physical or chemical.

The "cells" mentioned in the present invention refer to those having mitochondria, such as adipose-derived stem cells, mesenchymal stem cells, skeletal muscle cells, liver cells, kidney cells, fibroblasts, nerve cells, skin cells, blood cells, and the like.

The "blood product" mentioned in the present invention refers to a product prepared by using the blood as the raw material, and contains a certain amount of growth factors, such as PRP separated out from the whole blood, blood added with growth factors, or the like. The "certain amount" mentioned herein refers to an amount obtained according to well-known knowledge by persons of ordinary skill in the art to which the present invention pertains. For example, the number of platelets in the PRP disclosed in the present invention is at least 1,000,000/μl and the PRP contains the following growth factors: PDGF-BB (155.2±57.67 ng/ml), IGF-1 (236.07±222.1 ng/ml), TGF-β1 (488.76±240.77 ng/ml), VEGF (242.29±97.64 ng/ml), and bFGF (82.24±64.51 ng/ml).For another example, the content of the growth factors in the blood product mentioned in the present invention is at least 522.54 ng/ml, and the blood product is required to contain platelets of which the number is at least 1,000,000/μl.

The "administration" mentioned in the present invention refers to enabling the mitochondria disclosed in the present invention to contact the injured tendon part, and the way of contacting the injured tendon part is not limited to smearing, dripping, injecting, introducing, etc. Moreover, an external force, such as ultrasound waves, shockwaves, heating, or the like, is further utilized to strengthen or accelerate the uptake by the cells.

The "tendon injury-related disease" mentioned in the present invention refers to a disease resulting from tendon tears, reduced flexibility, and decreased force-bearing capacity, such as tendonitis. Because tendons exist between muscles and bones, the tendon injury-related disease can occur in various parts of the body having tendons. Clinically, there are different indication names according to different locations of the tendons, such as biceps tendinitis, rotator shoulder tendinitis, knee patellar tendinitis, Achilles tendinopathy, calcific tendinitis in a shoulder joint, etc.

The "joint disease" mentioned in the present invention refers to a disease caused by tendon inflammation or injury. That is, when the tendon is injured or inflamed, the ability to move where the tendon is located (i.e. the joint) may be impaired. Moreover, as the tendon injury or inflammation time increases, the chance of a joint lesion or joint disease is significantly improved. For example, if the tendon in the knee is injured, the knee movement ability, such as bending, walking, etc., may be affected. Therefore, if the part with a tendon injury can be rapidly repaired, the joint disease, such as a frozen shoulder, degenerative arthritis, knee arthritis, etc., caused by a long-term tendon injury can be effectively prevented.

In order to prove the effects of the technical features disclosed in the present invention, several examples are given below to describe the present invention in detail with reference to the accompanying drawings.

In the following examples, hydroxyurea (HU) is used as a cell proliferation inhibitor in a cell migration assay.

Example 1: Culture of Human Tendon Cells

The culture of human tendon cells was performed by using a TEN-1 growth medium (Tenocyte Growth Medium, zenbio). Before the culture of the human tendon cells, the culture dish was coated with 250 μg/ml matrix gel (Brand: Corning, Model: 354234). After treatment for 1 hour, the matrix gel was removed and the phosphate buffer solution was used for cleaning; and then the human tendon cells were cultured in a 37° C. incubator (having 5% carbon dioxide) with the TEN-1 growth medium coated with the matrix gel. When the human tendon cells grew to the completeness of 9, the cell culture medium was removed and the phosphate buffer solution was used for cleaning. Then, the phosphate buffer solution was removed and 0.25% trypsin was added in to react at 37° C. for 5 min. After reaction completion, the TEN-1 growth medium was added in to neutralize the trypsin, and centrifugation was performed at 1000 rpm for 5 min. The supernatant was removed after centrifugation; and a new TEN-1 growth medium was added and cell counting was performed, for use in subsequent examples.

Example 2: Preparation of PRP

Fresh blood was taken into a separator tube (Brand: BD, Model: REF362761) containing an anticoagulant, and was centrifuged at 1500-2000g for 10 mins. Then, the blood sample was divided into four layers, which are a red blood cell layer, separating gel, a white buffy coat layer (containing monocytes and platelets), and a slightly-yellow transparent plasma layer from bottom to top. The buffy coat and the plasma were collected; and the collected buffy coat layer and plasma layer were transferred to another separator tube and centrifuged at 900g for 10 min. After centrifugation, the top $\frac{2}{3}$ of the plasma was removed, and the remaining product was uniformly mixed to obtain the PRP.

The number of platelets in the PRP prepared in this example was more than 1,000,000/μl, and the PRP contained a variety of growth factors, such as PDGF-BB (155.2±57.67 ng/ml), IGF-1 (236.07±222.1 ng/ml), TGF-β1 (488.76±240.77 ng/ml), VEGF (242.29±97.64 ng/ml), and bFGF (82.24±64.51 ng/ml).

For use in the following examples, the prepared PRP was added to a cell culture medium at 5 percent by volume or to an animal solvent to be injected, to prepare a PRP solution with a volume percentage concentration of 5%.

Example 3: Preparation of Mitochondria

The human adipose-derived stem cells were cultured to obtain 1.5×108 cells, and the Duchenne phosphate buffer solution (DPBS) was used to flush the cells and then was removed. Trypsin was added in to react for 3 min, and then a stem cell culture liquid (Keratinocyte SFM (1×) liquid, bovine pituitary extract, or 10 wt % fetal calf serum) was added in to terminate the reaction. Afterwards, the cells were collected and centrifuged (600g for 10 min), and the supernatant was removed. Then, 80 ml IBC-1 buffer solution (the buffer solution is compounded of 225 mM mannitol, 75 mM sucrose, 0.1 mM EDTA, and 30 mM Tris-HCl with pH of 7.4) was added to the cells, and centrifugation was conducted after homogenization, to obtain a precipitate that was the mitochondria (referred to as a mitochondrial precipitate in the following description). 1.5 ml IBC-1 buffer solution and a proteolytic enzyme inhibitor were added to the mitochondrial precipitate, and then the mitochondrial precipitate was placed aside in a 4° C. environment, for use in the following examples.

Example 4: Injury Test for Tendon Cells (1)

The human tendon cells cultured in Example 1 were subcultured in a 24-well plate, where the concentration per well was 5×10+ cells/500 μL. After 8-hour culturing, the supernatant was removed and the phosphate buffer solution was used for cleaning. Afterwards, the phosphate buffer solution was removed, and 500 μLTEN-1 growth medium was added to each well to perform culturing for 8 hours. After culturing, hydrogen peroxide with a concentration of 300 μM was used for treatment. The supernatant was removed after 4-hour reaction, and the phosphate buffer solution was used for cleaning. Afterwards, the cells in different groups were treated according to the following different administration conditions: adding the PRP, adding the mitochondria (40 μg), and adding the mitochondria (40 μg) and the PRP. Afterwards, each group was cultured separately for 24 hours. After culturing completion, the phosphate buffer solution was used for cleaning, and then the TEN-1 growth medium (250 μL/well) containing 10% alamar Blue was added in to perform culturing for 3-4 hours in a 37° C. environment. After culturing completion, fluorescent signal measurement (Excitation/Emission: 560/590 nm) was performed, to obtain a result shown in FIG. 1.

It can be known from the result of FIG. 1 that, the survival rate of the human tendon cells (referred to as a blank group in the following description) not treated with hydrogen peroxide is 100.4±1.83%; the survival rate of the human tendon cells (referred to as an $H_2O_2$ group in the following description) that are treated with hydrogen peroxide but not administered with the mitochondria and/or PRP is 59.97+ 12.83%; the survival rate of the human tendon cells (referred to as an $H_2O_2$/PRP group in the following description) that are treated with hydrogen peroxide and further administered with the PRP is 80.12±9.19%; the survival rate of the human tendon cells (referred to as an $H_2O_2$/mitochondrial group in the following description) that are treated with hydrogen peroxide and further administered with the mitochondria is 85.22±11.46%; and the survival rate of the human tendon cells (referred to as an $H_2O_2$/PRP/mitochondrial group in the following description) that are treated with hydrogen peroxide and mitochondria and further administered with the mitochondria and PRP is 99.16±11.83%.

The foregoing results show that the cell survival rate of the $H_2O_2$ group is obviously reduced as compared with that of the blank group, which indicates that the hydrogen peroxide can indeed injure the human tendon cells and lead to death of the tendon cells. The cell survival rate of the group administered with the mitochondria or PRP is obviously higher than that of the group using the hydrogen peroxide, and the cell survival rate of the $H_2O_2$/mitochondrial group is higher than that of the $H_2O_2$/PRP group. That is, the mitochondria and the PRP can both alleviate the injury in tendon cells and reduce the cell death, but the mitochondria have a better alleviation effect for the injury in tendon cells. Moreover, the cell survival rate of the $H_2O_2$/PRP/mitochondrial group is almost equal to that of the blank group. It indicates that, when the human tendon cells are injured, the simultaneous administration of the mitochondria and the PRP can alleviate the injury in the human tendon cells and further can repair the injured human tendon cells, thus achieving the effect of treating the injured human tendon cells or the related diseases.

Example 5: Injury Test for Tendon Cells (2)

The process of this example was substantially identical with that in Example 4, but had the following differences. In this example, except the blank group, the human tendon cells in other groups were first treated with tBHP with a concentration of 300 μM, and were then cultured according to different administration conditions for different groups. After culturing completion, fluorescent signal measurement (Excitation/Emission: 560/590 nm) was performed, to obtain a result shown in FIG. 2.

Figure 2:
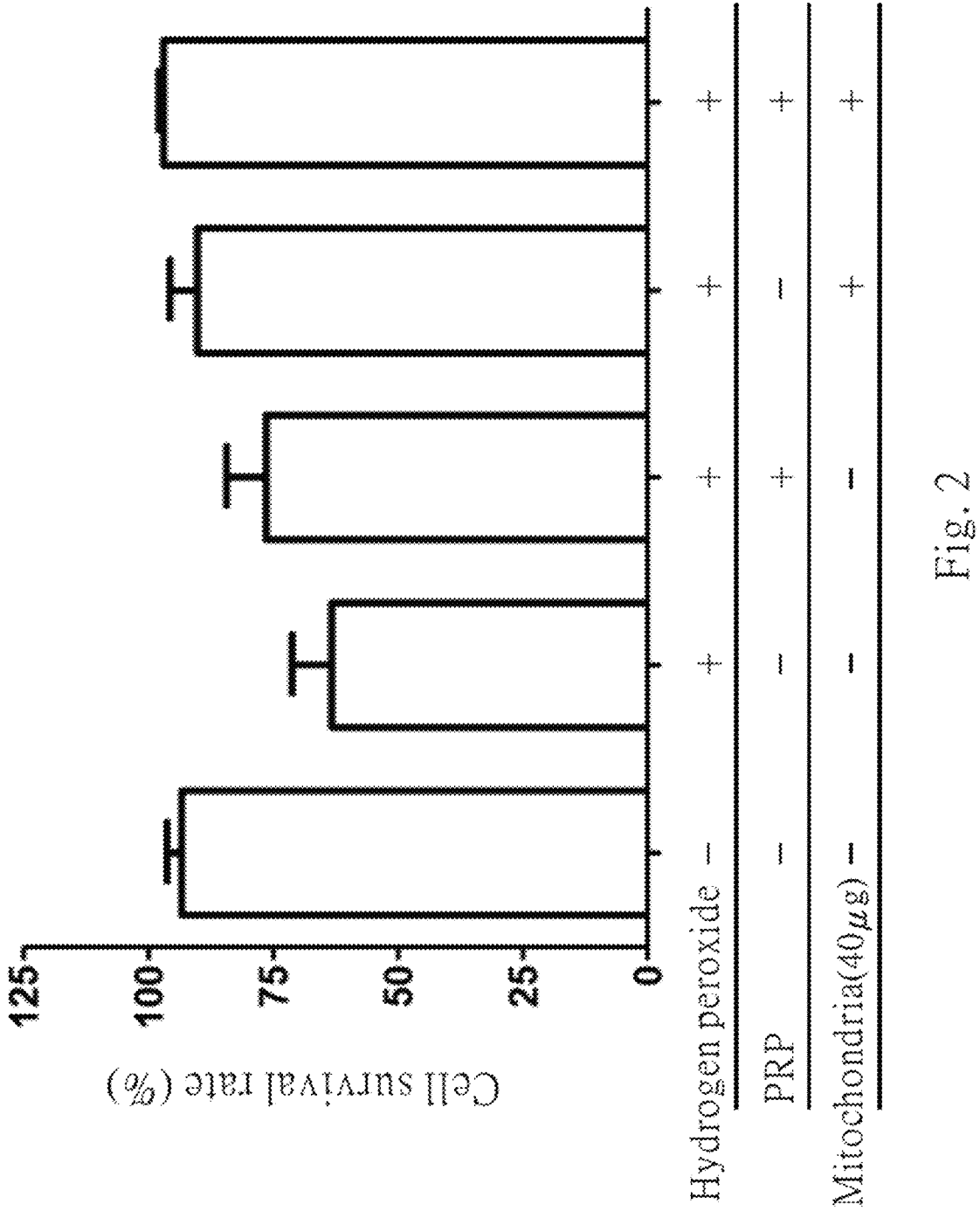
FIG. 2 shows an analysis result of a cell survival rate after the human tendon cells are treated with tert-butyl hydroperoxide (tBHP) and then cultured in different administration conditions.

It can be known from the result of FIG. 2 that, the survival rate of the human tendon cells (referred to as a blank group in the following description) not treated with tBHP is 93.38±7.65%; the survival rate of the human tendon cells (referred to as a tBHP group in the following description) that are treated with tBHP but not administered with the mitochondria and/or PRP is 63.3±16.03%; the survival rate of the human tendon cells (referred to as a tBHP/PRP group in the following description) that are treated with tBHP and further administered with the PRP is 76.4±19.55%; the survival rate of the human tendon cells (referred to as a tBHP/mitochondrial group in the following description) that are treated with tBHP and further administered with the mitochondria is 90.2±11.09%; and the survival rate of the human tendon cells (referred to as a tBHP/PRP/mitochondrial group in the following description) that are treated with tBHP/mitochondria and further administered with the mitochondria and PRP is 97±2.29%.

The cell survival rate of the tBHP group is obviously reduced as compared with that of the blank group, which indicates that tBHP can indeed injure the human tendon cells and lead to death of the tendon cells. The cell survival rate of the group administered with the mitochondria and/or PRP is obviously higher than that of the tBHP group, which indicates that the mitochondria and the PRP can both alleviate the injury in the human tendon cells induced by tBHP. In this case, the alleviation effect achieved by administration of only the mitochondria is superior to that achieved by administration of only the PRP. When the human tendon cells are injured after treatment with tBHP, the simultaneous administration of the mitochondria and the PRP can almost eliminate the injury in the human tendon cells, and the cell survival rate is almost equal to that of the blank group. That is, when the human tendon cells are injured, the simultaneous administration of the mitochondria and the PRP can effectively alleviate and repair the injury in the human tendon cells, thus promoting or accelerating the treatment of the injury in the human tendon cells or the related diseases.

Example 6: Migration Assay of Tendon Cells

The tendon cells were cultured in a 24-well plate at a concentration of $5 \times 10^4$ cells/500 μL for 24 hours. When the cell completeness reached 9, the phosphate buffer solution was first used to clean the cells, and then a straight wound of a fixed width was scraped in the middle of the cell. The TEN-1 growth medium and cells in suspension were removed and a mixed cell culture liquid (90% DMEM/F12+ 10% TEN-1 growth medium) containing 10 μM hydroxyurea was used to replace the original medium, and then the cells were cultured for 24 hours in the following different conditions separately according to an assay design: adding 40 μg mitochondria, adding 5% PRP, and adding 5% PRP and 40 μg mitochondria. After culturing, the repair and healing of the wound was observed and analyzed, to obtain a result shown in FIG. 3.

Figure 3A:
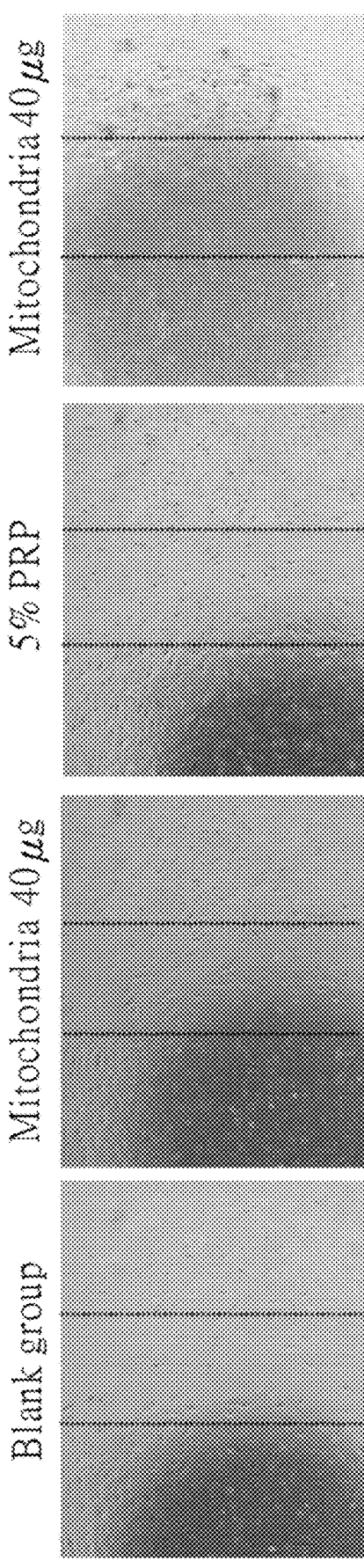
FIG. 3A shows a result of observing a cell migration assay after the human tendon cells are treated in different conditions.

It can be known from the result of FIG. 3A that, as compared with the blank group not administered with any medicine, the human tendon cells administered with the mitochondria, the PRP, or the PRP and mitochondria have a better repair effect. Moreover, it can be known from the result of FIG. 3B that, the cell migration number in the blank group is 100±27.58; the cell migration number in the group treated with the mitochondria is 211.31±42.18; the cell migration number in the group treated with the PRP is 221.6±56.61; and the cell migration number in the group treated with both the PRP and the mitochondria is 302.06±84.97.

Figure 3B:
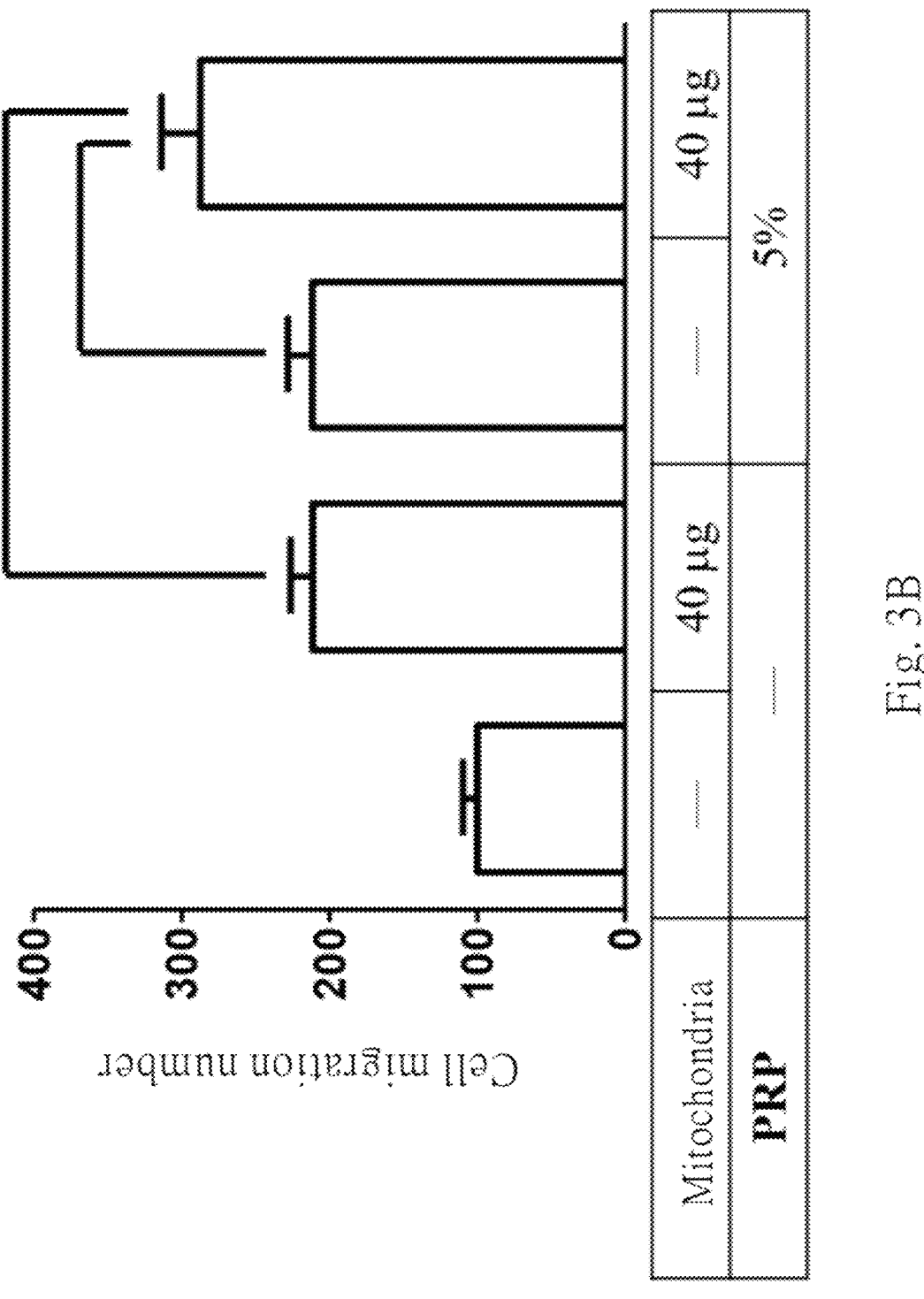
FIG. 3B shows a statistical analysis result of a cell migration assay after the human tendon cells are treated in different conditions.

The results of FIGS. 3A and 3B show that, the administration of only the mitochondria to the injured human tendon cells can promote the wound healing of the tendon, and its healing effect is equivalent or even superior to that achieved by the administration of only the PRP. If the mitochondria and the PRP are simultaneously administered to the injured human tendon cells, the wound healing rate can be accelerated. That is, the mitochondria or the composition containing the mitochondria disclosed in the present invention can indeed promote or accelerate the healing of the tendon wound, thus achieving the effect of accelerating the repair of the injured tendon cells or treating the tendon lesion.

Example 7: Experiment on Animals 12-week-old female Sprague-Dawley (SD) mice were raised in a 22±2° C. environment with the humidity ranging from 50% to 70%, and a tendon injury was induced in each mouse by using type 2 collagenase. Then, their tendon strength was observed and analyzed after treatment in different conditions.

In detail, the mice in each group were first anesthetized, the hair around their shoulder joints was shaved, and disinfection was performed with 70% alcohol. Then, the type 2 collagenase was injected into the supraspinatus tendon between coracoids and clavicle of each mouse with a needle and a syringe at an angle of 45 degrees, where the injection was required to be completed at a concentration/dose of 80 U/8 ul within 1 min. The day when the injection of type 2 collagenase was performed and completed was set to the $0^{th}$ day of the experiment, and the tendon injury status of each mouse was observed and estimated from the $0^{th}$ day of the experiment. On the $3^{rd}$ day of the experiment, the injury was treated in different administration conditions for the different groups, including no administration, administering the mitochondria (15 μg), administering the PRP (5 vol %), and administering the mitochondria (15 μg) and the PRP (5 vol %). The tendon strength was analyzed on the $7^{th}$ day and the $14^{th}$ day of the experiment, and in this example, the tendon injury status was estimated and the tendon strength was analyzed by using a vertical automatic tester (JSV-H1000). That is, after the mice that have completed the experiment were sacrificed, the supraspinatus tendons together with the humeri were taken down and placed on the vertical automatic tester to take a test at a rate of 10 mm/min, where a force that broke the tendon was the maximum strength of the mouse tendon. The results of this example are shown in tables 1 and 2.

It can be known from the result of table 1 that, on the 3rd day after the type 2 collagenase is administered, the tendon inflammation and injury can be observed and the tendon strength is obviously reduced, which indicates that the type 2 collagenase can indeed induce the tendon inflammation and swelling. On the $7^{th}$ day and the $14^{th}$ day, it is observed that the tendon inflammation and swelling are both alleviated, and the tendon strength is gradually improved but still less than half of the strength on the day (the 0th day) of injection. As shown in table 2, it can be known from the results of the tendon strength on the $7^{th}$ day and $14^{th}$ day of the experiment that, the mouse tendon inflammation and injury status in which the mitochondria and/or PRP are/is administered is better than that without administration of any medicine, and moreover, the tendon strength recovers better. Further, the tendon strength has the best recovery effect in the case where the PRP and the mitochondria are simultaneously administered.

The results indicate that, the mitochondria or a composition containing the mitochondria, such as a composition compounded of the mitochondria and PRP, disclosed in the present invention can indeed alleviate the tendon inflammation and swelling and further can promote the tendon repair efficiency. Therefore, the injured tendon can be restored to its strength and elasticity in a short period of time, thus achieving the effect of treating or preventing the tendon injury-related diseases.

TABLE 1

| Estimation results of tendon strength of mice in a tendon injury pattern (type 2 collagenase is only injected and mitochondria and/or PRP are/is not administered) | | | | |
| --- | --- | --- | --- | --- |
| Experiment day | the $0^{th}$ day | the $3^{rd}$ day | the $7^{th}$ day | the $14^{th}$ day |
| Maximum tendon strength (N) | 33.32 ± 2.13 | 5.32 ± 1.21 | 9.13 ± 1.19 | 16.13 ± 2.06 |

TABLE 2

| Results of a tendon strength test during the experiment for mice in each group | | | |
| --- | --- | --- | --- |
| | Tendon strength (N) | | |
| Experiment day | the $3^{rd}$ day | the $7^{th}$ day | the $9^{th}$ day |
| Group administered with collagenase (the blank group) | 5.32 ± 1.21 | 9.13 ± 1.19 | 16.13 ± 2.06 |
| Group administered with PRP | | 12.83 ± 1.28 | 17.96 ± 1.73 |
| Group administered with mitochondria | | 13.27 ± 1.36 | 18.28 ± 1.94 |
| Group administered with mitochondria and PRP | | 15.31 ± 2.21 | 21.36 ± 2.26 |

What is claimed is:

1. A method for treating and/or preventing a tendon injury-related disease, comprising administering to a subject an effective amount of a composition, wherein the composition includes mitochondria and platelet-rich plasma (PRP);

the dose of the mitochondria in the composition is at least 15 µg; and the concentration of the platelet-rich plasma is 5% (v/v) and more.

2. The method for treating and/or preventing a tendon injury-related disease of claim 1, wherein the tendon injury-related disease is tendonitis.

3. The method for treating and/or preventing a tendon injury-related disease of claim 1, wherein the tendon injury-related disease comprises a symptom of tendon inflammation or swelling.

4. The method for treating and/or preventing a tendon injury-related disease of claim 1, wherein the tendon injury-related disease is a tendon lesion.

5. The method for treating and/or preventing a tendon injury-related disease of claim 1, wherein the dose of the mitochondria in the composition ranges from 15 µg to 80 µg.

6. The method for treating and/or preventing a tendon injury-related disease of claim 1, wherein the content of the growth factor in the platelet-rich plasma is 522.54 ng/ml and more.

7. The method for treating and/or preventing a tendon injury-related disease of claim 1, wherein the platelet-rich plasma includes at least 1,000,000 platelets/µl.

8. The method for treating and/or preventing a tendon injury-related disease of claim 1, wherein the platelet-rich plasma includes 155.2±57.67 ng/ml of PDGF-BB, 236.07±222.1 ng/ml of IGF-1, 488.76±240.77 ng/ml of TGF-β1, 242.29±97.64 ng/ml of VEGF and 82.24±64.51 ng/ml of bFGF.

9. The method for treating and/or preventing a tendon injury-related disease of claim 1, wherein the mitochondria have an intact structure and are obtained by the following steps:

(a) collecting cells comprising mitochondria;

(b) subjecting the cells to homogenization and centrifugation, and collecting the resulting precipitate, wherein the precipitate is the mitochondria.

10. The method for treating and/or preventing a tendon injury-related disease of claim 1, wherein the tendon injury-related disease is a joint disease or a ligament injury-related disease, which is caused by a tendon injury or tendon inflammation.

11. The method for treating and/or preventing a tendon injury-related disease of claim 1, wherein the composition further includes a blood product, which includes at least one of the following growth factors: PDGF-BB, IGF-1, TGF-β1, VEGF, and bFGF.

12. The method for treating and/or preventing a tendon injury-related disease of claim 1, wherein the dose of the mitochondria in the composition ranges from 30 µg/ml to 160 µg/ml.

* * * * *